United States Patent [19]

O'Brien et al.

[11] Patent Number: 4,580,577
[45] Date of Patent: * Apr. 8, 1986

[54] METHOD AND APPARATUS FOR COLLECTING SALIVA

[76] Inventors: Joseph O'Brien; Paul Brown, both of c/o MetPath Inc., One Malcolm Ave., Teterboro, N.J. 07608

[*] Notice: The portion of the term of this patent subsequent to Dec. 6, 2000 has been disclaimed.

[21] Appl. No.: 506,443

[22] Filed: Aug. 9, 1983

Related U.S. Application Data

[60] Division of Ser. No. 331,890, Dec. 17, 1981, Pat. No. 4,418,702, which is a continuation-in-part of Ser. No. 224,306, Jan. 12, 1981, abandoned.

[51] Int. Cl.⁴ .............................................. A61B 10/00
[52] U.S. Cl. ................................... 128/760; 604/224; 604/226; 604/317; 100/131; 73/864.91; 422/101; 422/102

[58] Field of Search .............. 128/760, 762, 769, 296, 128/275, 749, 759; 433/136; 422/101, 102; 604/406, 358, 317, 224, 226; 73/864.91, 864.92

[56] References Cited

U.S. PATENT DOCUMENTS

| | | | |
|---|---|---|---|
| 972,686 | 7/1910 | Foster | 128/236 |
| 2,905,169 | 5/1959 | Nieburgs | 128/756 |
| 3,518,164 | 4/1970 | Andelin et al. | 128/760 X |
| 4,014,322 | 8/1977 | Shah | 128/760 |
| 4,114,605 | 6/1978 | McGhee et al. | 128/760 |
| 4,418,702 | 12/1983 | Brown et al. | 128/760 |

Primary Examiner—Kyle L. Howell
Assistant Examiner—John C. Hanley

[57] ABSTRACT

A method and apparatus for collecting saliva from a test subject comprises providing a flavored absorbent mass, such as a sponge, for mastication and charging with saliva and then expressing the saliva from the mass. Apparatus for this method comprises a barrel-piston arrangement in association with a specimen vial for storage until diagnostic testing.

4 Claims, 2 Drawing Figures

U.S. Patent
Apr. 8, 1986
4,580,577
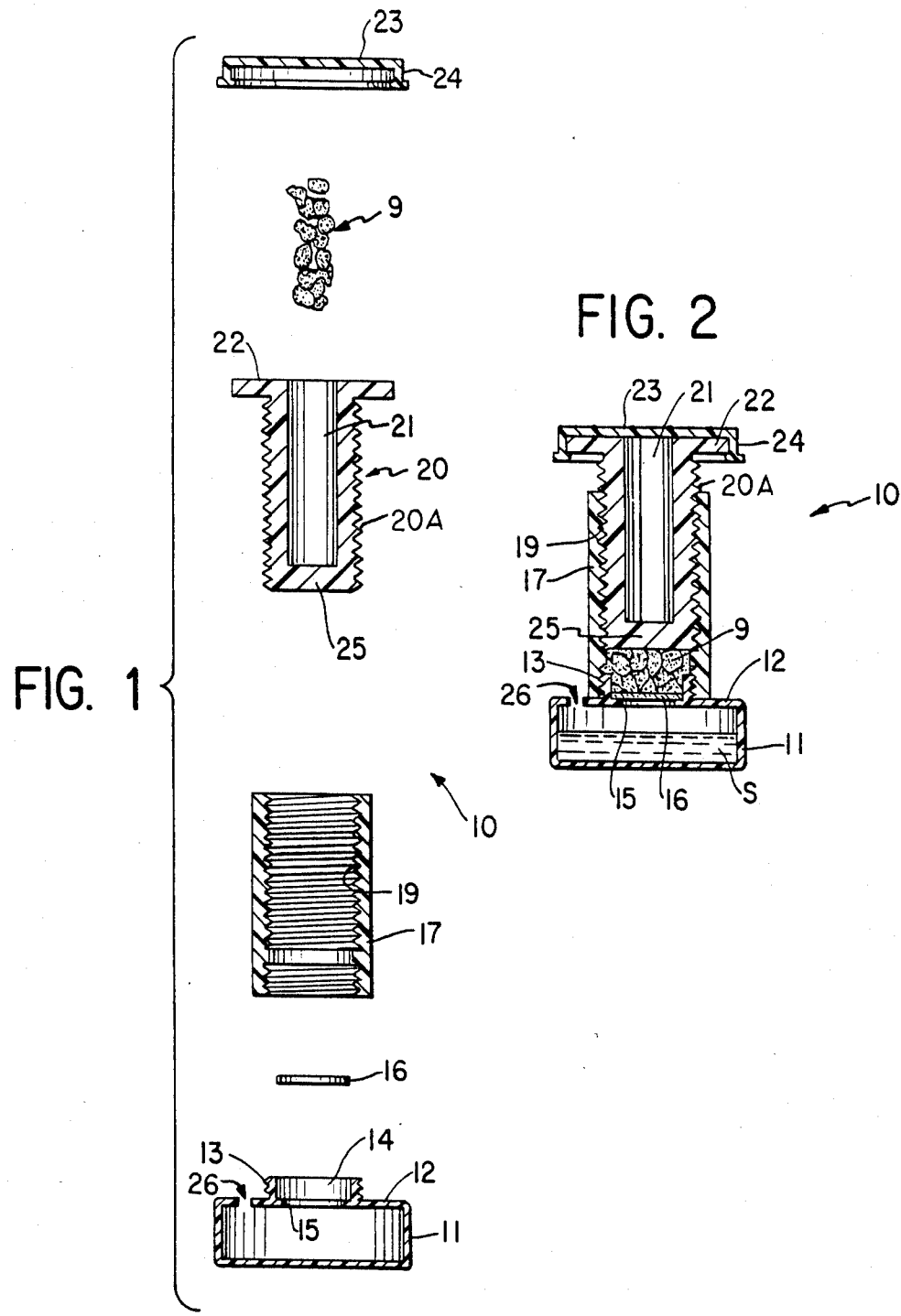

4,580,577

METHOD AND APPARATUS FOR COLLECTING SALIVA

This is a division of application Ser. No. 331,890 filed Dec. 17, 1981, now U.S. Pat. No. 4,418,702, which is a C-I-P of application Ser. No. 224,306 filed Jan. 12, 1981 abandoned.

BACKGROUND AND SUMMARY OF THE INVENTION

Standardized specimen receptacles for collecting, storing and transporting body fluids, such as blood or urine, for later use in diagnostic testing are common and well-known. It is an object of the present invention to provide a new and improved method and apparatus for collecting saliva.

SUMMARY OF THE INVENTION

The novel method for collecting saliva specimens comprises providing a test subject with an absorbent flavored mass to be placed in the mouth until a quantity of saliva has been absorbed. The absorbed saliva is then expressed from the mass into a receiving apparatus. The apparatus of the invention comprises a barrel and screw jack-piston for containing and compressing the mass in association with a specimen vial for holding the expressed saliva. A preservative is included within the specimen vial to preserve the saliva specimen and to prevent its contamination before diagnostic testing.

For a more detailed understanding of the present invention and for a greater appreciation of its attendant advantages, reference should be made to the following detailed description taken in conjunction with the accompanying drawings.

DESCRIPTION OF THE DRAWINGS

FIG. 1 is an exploded view of the apparatus embodying the principles of the invention, and FIG. 2 is a front elevational view of the new apparatus.

DETAILED DESCRIPTION OF THE INVENTION

In accordance with the principles of the invention, an absorbent mass 9 is provided of a size and shape to fit easily within the test subject's mouth for mastication, but not so small as to present a risk of being swallowed. This mass 9 may be made, for example, of cellulose sponge or absorbent thermo-plastic foam, such as a polyester or polyurethane foam.

In FIG. 1, the specimen collector 10 of the present invention appears in exploded form. The base is a cylindrical specimen vial 11, in which the saliva specimen will be stored until tested. The vial 11 has a top wall 12 supporting an upwardly projecting cylindrical threaded flange 13 defining an aperture 14. A horizontal projecting flange 15 of the vial 11 supports a removable filter disc 16 which completely covers the aperture 14.

Threaded upon the flange 13 is a hollow, cylindrical barrel 17. The interior of the barrel 17 is of sufficient volume to hold the mass 9 when saturated. Interior coarse threads 19 in the barrel 17 matingly receive a threaded piston 20. Specifically, the piston 20 itself has a hollow interior 21, open at the fingergrip top 22, to serve as a storage space for the mass 9. The piston 20 has a compression head 25 at its bottom surface. A snap-on cover 23, having a resilient downwardly extending flange 24, engages the fingergrip top 22 and sealing into the interior 21 from contamination by contact with the outside atmosphere.

In accordance with the invention and to encourage the test subject to salivate while chewing on the mass 9, the mass 9 may be impregnated with a flavor, such as chocolate or cherry, the flavoring agent being inert and digestible. This will also help overcome any reluctance on the part of the test subject to place the mass 9 in his or her mouth.

To obtain the saliva specimen, the procedure of the invention is as follows: The cover 23 is snapped off and the mass 9 is removed from the interior 21. The test subject places it in his or her mouth and masticates it until it has become saturated with saliva. The piston 20 is unscrewed from the extruder barrel 17. The saturated mass is deposited in the extruder barrel 17 and the piston 20 is inserted and threaded down until the saliva specimen has been expressed from the mass 9 by the action of the compression head 25 against the filter disc 16 and has passed into the specimen vial 11. Ambient air within the confines of the barrel will be forced out through the space between threads 19 and the threads 20 on the plunger, as will be understood. When the fit between strands 19,20a is tight rather than loose, a relief vent 26 is formed in vial 11. The filter disc 16 prevents particles of the mass 9 or other detritus and/or bacteria from being collected, and may be held in place by adhesive at the periphery or by mechanical locking means. The saliva specimen is then stored in the vial 11 until it is used for diagnostic testing. The cap 23 may be sized and configured, if desired, to be used to seal the vial 11 rather than using a separate cap.

To preserve the specimen until testing, the specimen vial may be provided with a preservative. Alternatively, if desired or necessary, a reactant for an immediate processing step may be provided.

The elements of the specimen collector may all be made of inexpensive plastic making the collector readily disposable after a single use. Moreover, the plastic construction of the specimen collector enables it to be safely and reliably shipped or mailed to laboratories for testing.

It will be understood that while the embodiment described has been directed toward human test subjects, it may be directed toward use with animal test subjects if means for recovering the sponge from the animal's mouth is provided, e.g., by mounting the sponge upon a rod.

Thus, the method for collecting saliva samples is effective and systematic and the specimen collector is easy to manipulate and inexpensive to manufacture.

I claim:

1. Apparatus for collecting a saliva specimen from a test subject, comprising
   (a) a masticatable, mass of saliva-absorptive material in the form of a cellulose sponge means;
   (b) collection means having an entrance aperture providing access to the interior thereof;
   (c) means for expressing absorbed saliva from said mass into said collection means comprising a tube within which said mass may be disposed, a barrier formed at one end of said tube, said barrier including an exit aperture of small enough dimension to prohibit the passage of said mass therethrough;
   (d) a movable plunger fitting within said tube and having a cavity formed therein for storing said sponge means;

(e) said exit aperture being in alignment with said entrance aperture;
(f) first screw threads formed on interior surfaces of said tube;
(g) second screw threads formed on the exterior surfaces of said plunger and engaging said first screw threads; and
(h) a removable cover completely spanning said cavity and resiliently engaging said plunger.

2. Apparatus according to claim 1, wherein said barrier comprises a removable filter.

3. Apparatus according to claim 1, wherein said mass is flavored.

4. A method for collecting a volume of saliva as a specimen from a test subject, comprising the steps of (a) storing a mass of saliva absorptive material within collection means adapted to express and contain saliva;
(b) removing said mass from said collection means and providing said mass to said subject for mastication and for charging with a volume of saliva;
(c) placing said charged mass within a hollow cylindrical barrel, having two ends, in said collection means;
(d) pressing said charged mass against a filter covering one end of said barrel by inserting a piston telescopically into the other end of said barrel;
(e) expressing said saliva from said charged mass through said filter into a collection area of said collection means adapted to receive said saliva.

* * * * *